(12) United States Patent
Goshert

(10) Patent No.: US 6,623,487 B1
(45) Date of Patent: Sep. 23, 2003

(54) TEMPERATURE SENSITIVE SURGICAL FASTENER

(75) Inventor: David R. Goshert, Pierceton, IN (US)

(73) Assignee: Biomet, Inc., Warsaw, IN (US)

( * ) Notice: Subject to any disclaimer, the term of this patent is extended or adjusted under 35 U.S.C. 154(b) by 95 days.

(21) Appl. No.: 09/782,725

(22) Filed: Feb. 13, 2001

(51) Int. Cl.⁷ .............................................. A61B 17/56
(52) U.S. Cl. .............................. 606/72; 606/77; 606/70
(58) Field of Search ........................... 606/70, 72, 76, 606/77; 411/501; 623/16.11

(56) References Cited

U.S. PATENT DOCUMENTS

| 2,994,933 A | * | 8/1961 | Wolfe ............................ 16/2.1 |
| 4,590,928 A | * | 5/1986 | Hunt et al. ...................... 606/72 |
| 5,084,050 A | * | 1/1992 | Draenert ......................... 606/77 |
| 5,120,175 A | * | 6/1992 | Arbegast et al. ............. 411/501 |
| 5,290,281 A | * | 3/1994 | Tschakaloff ................... 606/28 |
| 5,569,250 A |   | 10/1996 | Sarver et al. |
| 5,578,034 A | * | 11/1996 | Estes ............................. 606/61 |
| 5,779,706 A | * | 7/1998 | Tschakaloff ................... 606/69 |
| 5,941,901 A | * | 8/1999 | Egan ............................ 606/232 |
| 6,206,883 B1 | * | 3/2001 | Tunc ............................. 606/77 |
| 6,221,075 B1 | * | 4/2001 | Tormala et al. ................ 606/77 |
| 6,332,885 B1 | * | 12/2001 | Martella ....................... 428/330 |
| 6,471,706 B1 | * | 10/2002 | Schumacher et al. ......... 606/69 |
| 6,485,504 B1 | * | 11/2002 | Johnson et al. ............. 606/216 |
| 2002/0016596 A1 | * | 2/2002 | Cooper ......................... 606/77 |

* cited by examiner

*Primary Examiner*—Henry Bennett
*Assistant Examiner*—Kathryn Ferko
(74) *Attorney, Agent, or Firm*—Harness, Dickey & Pierce, P.L.C.

(57) ABSTRACT

A temperature sensitive fastener is formed by extruding, then pulforming and then machining the fastener. The pulforming forms uniaxial longitudinal stress in the fastener. The fastener has a head and a shank. The fastener is positioned in an osteosynthesis plate so that an opening in the plate is substantially coaxial with the bore on the bone. The shank extends into the opening in the plate and into one of the bone portions. The head overlies the plate. The fastener is heated to relieve the stresses in the shank so that the shank expands to frictionally secure the shank to the bore without deforming the material and thereby preventing thermal necrosis.

17 Claims, 1 Drawing Sheet

TEMPERATURE SENSITIVE SURGICAL FASTENER

BACKGROUND

1. Field of the Invention

The present invention relates generally to a surgical fixation device for bone fractures, and more particularly, to a fastener and method of forming the fastener for securing a fixation plate to a bone.

2. Discussion of the Related Art

Fixation or osteosynthesis plates are used to promote the proper healing of bones especially for the realignment of separated, fractured or dislocated bone segments. Any relative movement between the bone segments may result in a failure to join the separated bone segments or an extension of time to heal the bone fracture. Therefore, it is desirable to prevent any relative movement of the bone segments at the fracture site. This involves the fixation of the separated bone segments through the use of fixation plates and fasteners to bridge the fracture and stabilize the bone segments.

Some prior art devices fasten a resorbable fixation plate to the bone segments by inserting metal bone screws through the plate and into a hole that is drilled and tapped into the bone itself. This technique provides rigid securement to the fixation plate to the bone. Examples of fixation plates which use this technique include U.S. Pat. No. 5,578,034 and U.S. Pat. No. 5,569,250.

While this technique has been used for quite some time, there are several disadvantages with resorbable fixation devices that use metal bone screws. In this regard, since a surgeon is required to both drill and tap threads into a bone, the surgeon is also required to make sure that the depth of the tapped hole and the length of the metal screw be within a precise tolerance. If the tapped hole is shorter than the screw, the screw will not seat properly and the fixation plate may not be adequately secured to the bone. This situation can be rectified by removing the screw and re-drilling and tapping the bone. However, if the screw breaks during its removal, it may require the drilling and tapping of another hole at another site or repositioning the fixation plate. Another undesirable consequence of using metal screws is the need for an additional surgical procedure to remove the screws after the bone fracture has healed.

Another approach used in the prior art to solve this problem is the use of resorbable fixation plates and resorbable screws. Examples of resorbable screws are U.S. Pat. Nos. 5,569,250; 5,290,281; and 4,550,449. However, resorbable screws are sometimes prone to cross-threading and/or breaking during insertion.

A third approach used to solve these disadvantages involves forming a fastener with a shank that is heated to a temperature that permits the material to melt and deform so as to form a tight fit within the hole drilled in the bone. An example of this approach is shown in U.S. Pat. No. 6,080,161. This fastener, however, requires a substantial amount of heat to melt and deform the shank which can cause thermal necrosis of the tissues surrounding the bone. This is undesirable and can inhibit the healing process.

The present method seeks to overcome the above mentioned disadvantages by forming a simple to use surgical securing device which after insertion into the bone, is heated to relieve uniaxial stresses in the material used to make the securing device so that the securing device distends to fill the bore and frictionally secure the fixation plate to the bone as well as reducing the incidence of thermal necrosis of the tissues surrounding the bore.

SUMMARY OF THE INVENTION

In accordance with the teachings of the present invention, a fastener and a method for forming a fastener adapted to secure a osteosynthesis plate to a plurality of bone portions are disclosed.

In the preferred embodiment, the fastener includes a head which engages an opening in the fixation plate and a shank attached to the head. The shank is disposed in a bore formed in the bone. The shank is constructed of a material having uniaxial longitudinal stresses formed therein. The stresses in the material, when heated, are relieved whereby the shank expands radially to frictionally secure the shank in the bore without deforming the material.

In the preferred method, the fastener is first formed by extruding a polymeric material. Next, the extruded polymeric material is pulformed. Then, the pulformed material is machined to form a fastener. The fastener has a head and a shank. The shank has uniaxial longitudinal stress formed therein. Next, a fixation plate is positioned so that an opening in the plate is substantially coaxial with the bore. The fastener is then disposed into the substantially coaxial bore so that the shank extends into one of the bone portions and the head overlies the fastener plate. Then, the fastener is heated to relieve the stresses in the shank whereby the shank expands radially to frictionally secure the shank in the bore.

The present invention has the advantage of providing a fastener, using pre-stressed material to secure a fixation plate to a bone portion with a bore, that is simple to use and is heated to relieve the stresses in the material in order to permit the material to expand radially to fill the bore and frictionally secure the fixation plate to the bone. As a result, the present invention reduces the incidence of thermal necrosis of the tissues surrounding the bore. Also, the disadvantages associated with the currently available surgical fasteners have been substantially reduced or eliminated.

It is therefore an object of the present invention to provide an easy to use and effective fastener for attaching a fixation plate to the bone by heating a uniaxially pre-stressed fastener to relieve uniaxial stresses in the shank and dilate the shank in order to frictionally engage the bore so that necrosis of the surrounding tissues is prevented.

It is a further object of the present invention to provide a method of forming a uniaxially pre-stressed fastener that permits securing a fixation plate to bone by annealing the fastener to relieve uniaxial stresses and to radially expand the shape of the fastener to frictionally engage the bore.

For a more complete understanding of the invention, its objects and advantages, reference should be made to the following specification and to the accompanying drawings.

BRIEF DESCRIPTION OF THE DRAWINGS

The drawings, which form an integral part of the specification, are to be read in conjunction therewith, and like reference numerals are employed to designate identical components in the various views.

DETAILED DESCRIPTION OF THE INVENTION

The following description of the preferred embodiments concerning a surgical fastener and the process of forming the fastener which is adapted for securing a fixation plate having a plurality of openings to a plurality of bone portions with a bore, are merely exemplary in nature and are not intended to limit the invention or its applications or uses. Moreover, while the present invention is described in detail below generally with respect to a resorbable fastener, it will be appreciated by those skilled in the art that the present invention is not limited to only an resorbable fastener and may be applied to other material fasteners which are not resorbable as discussed herein.

Figure 1:
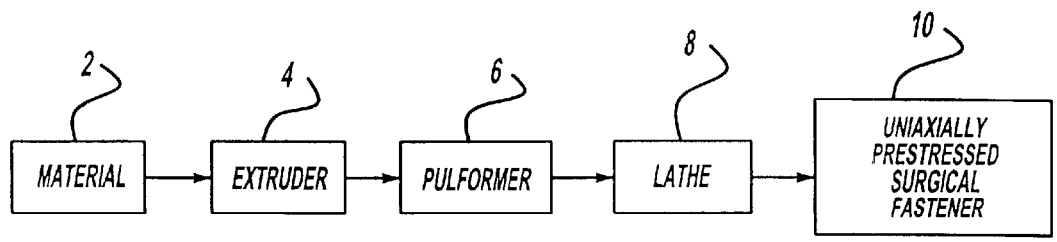
FIG. 1 is a schematic block diagram of the method of forming the surgical fastener according to the teachings of the present invention.

FIG. 1 shows the process of making the surgical fastener or rivet generally designated by the numeral 10. The process includes processing a material 2 in a conventional extruder 4 to form an extrudate. The extrudate is then placed in a conventional pulformer 6 which applies a strong pulling force to the extrudate profile by a series of grippers or puller devices (not shown). The pulformer 6 stretches the material 2 to produce uniaxial longitudinal stress in the solid pultraded profile. Next, the pre-stressed pultraded profile is machined by a conventional machining or lathe device 8 to form the pre-stressed surgical blank or fastener 10. The fastener 10 includes an elongated shank 12 having an upper end 14 and a lower end 16 (see FIG. 4). While the fastener 10 is shown as having a round profile, those skilled in the art will recognize that the shank may take on other suitable shapes such as polygonal, oval, triangular, square and rectangular.

The pre-stressed surgical fastener 10 is preferably formed of a biocompatible material 2 such as a non-reinforced lactide and glycolide copolymer composition that is non-oriented. The copolymer is made from about 70%–85% m lactide moieties and from about 15%–30% m glycolide moieties having a molecular weight of generally between 30,000 and 100,000. Such a copolymer is sold under the name Lactosorb® which may be obtained from Walter Lorenz Surgical, Inc. of Jacksonville, Fla. Alternatively, other biodegradable lactide and comonomer blends may be used, such as disclosed in U.S. Pat. No. 5,550,449 which is hereby incorporated by reference. Further alternatively, the material 2 may be a non-absorbable material such as polypropylene.

Figure 2:
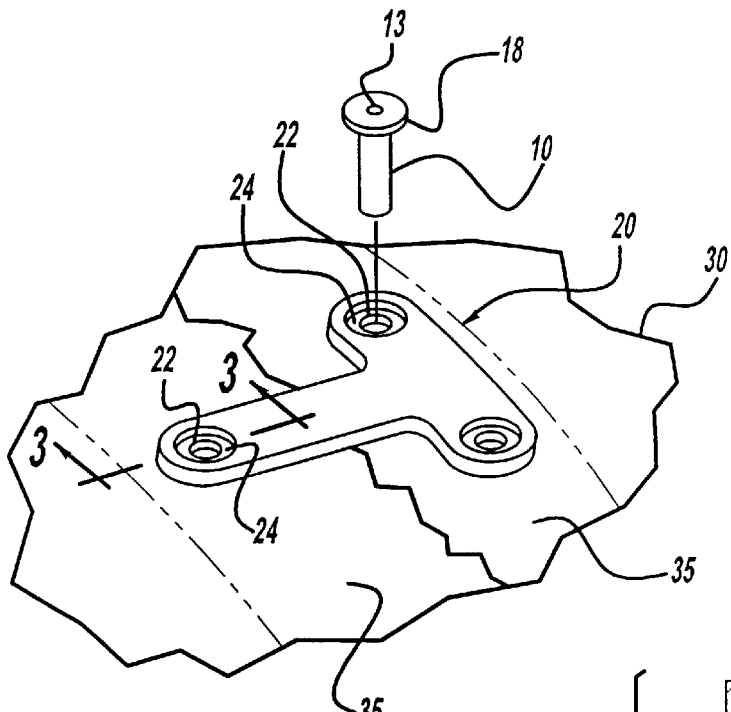
FIG. 2 is a top view showing a surgical fixation plate adjacent to a portion of a bone with a fracture prior to the surgical fastener being inserted therein.

As shown in FIG. 2, the fastener 10 secures an osteosynthesis plate 20 having a plurality of openings 22 to a plurality of bone fragments or segments 35. The osteosynthesis plate 20 is preferably bioresorbable. The plate 20 is contoured to fit the particular application as is known in the art. The plate 20 generally has a plurality of holes or openings 22 to accommodate surgical fasteners 10. Those skilled in the art will appreciate that the osteosynthesis plate 20 may take many shapes and sizes. The plate 20 is not part of this invention. The plate 20 has a preferably thin cross sectional area so as to cause a minimum protrusion above the bone surface to which it is affixed. The plate 20 may optionally be made of a non-absorbable material known in the art. The opening 22 in the osteosynthesis plate 20 may further include a recessed upper face 24. The plate 20 is then operable to accept a plurality of surgical fasteners 10 therein.

Figure 3:
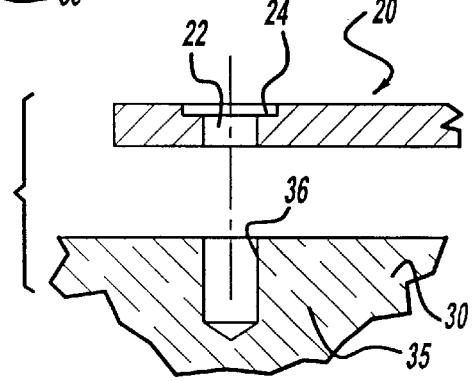
FIG. 3 is a partial cross-sectional view along 3—3 of FIG. 2.

As shown in FIG. 3, the contoured resorbable plate 20 is positioned by the surgeon who forms a hole 36 into the bone fragment 35 underlying the plate 20 such as by drilling (not shown). The surgeon may also form a hole in the resorbable plate 20 itself or, as an alternative, the resorbable plate 20 may include a preformed hole. Such drilling is performed through processes well known by those skilled in the art. The osteosynthesis plate 20 is positioned so that an opening 22 in the plate 20 is substantially coaxial with the hole 36 in the bone fragments 35.

Figure 4:
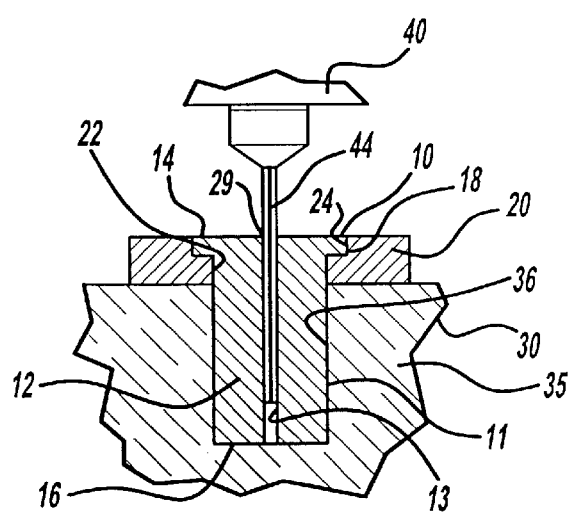
FIG. 4 is a partial cross-sectional view similar to FIG. 3 but with the annealed surgical fastener of the present invention frictionally engaging in the bore to the bone.

The fastener 10 is adapted for insertion into an opening 22 into the bioresorbable plate 20 and then into a hole 36 formed in a portion of the bone fragment 35. The upper end 14 of the shank 12 has a head 18 which engages at least a portion of one of the fastener openings 22 formed in the plate 20. The head 18 may take various shapes and forms, as is well known in the prior art. The head 18 may optionally be made with a diameter that is larger than the shank 12 as is shown in FIGS. 2 and 4.

The fastener 10 is inserted into the substantially coaxial hole 36 in the bone 30 that is oversized by 0.0005 to 0.0025 inches greater than the outer diameter 11 of the shank portion 12 and preferably 0.001 to 0.002 inches greater. This is not to be taken as a limitation of the invention. The outer diameter 11 is smaller than the inner diameter of the bore 36 because the thin, damaged bone structure may not be able to tolerate a press fit of the fastener 10 in the bore 36. Thus, the outer diameter 11 of the shank 12 is less than or almost equal to the outer diameter of the hole 36 in the bone fragment 35. The shank portion 12 of the fastener 10 extends into the bone 30 and the head portion 18 overlies the resorbable plate 20. The pre-stressed fastener 10 is heated to a temperature sufficient to relieve or anneal the stresses in the fastener. When the fastener 10 is relieved of its stresses, the fastener 10 expands radially and at the same time, the axial length of the fastener is reduced somewhat. Thus the fastener 10 dilates or expands radially to frictionally engage the walls of the bore 36 and to secure the plate 20 to the bone 30 without substantial deformation of the fastener 10.

The shank 12 is also adapted to accommodate a heat source 40. When the pre-stressed fastener 10 is heated to a temperature that relieves the stresses in the fastener, the periphery of the shank 12 dilates and expands radially to frictionally engage the hole formed in the bone as is shown in FIG. 4. Because the pre-stressed fastener 10 is only relieved of its stresses by the heat, the shank portion does not melt or undergo any substantial deformation other than dilation. As used herein, the word dilate is used to describe the process where an article that has been uniaxially longitudinally pre-stressed is then exposed to heat to relieve the micro stresses in the material thereby, causing the outer expansion of its periphery without melting or deforming the article. Annealing, as used herein, is a term used to denote a heat treatment process wherein the microstructure and stresses in the material are altered without melting or deforming the article.

The heat source 40 is inserted into an aperture 13 in the shank so as to anneal the fastener 10 by suitable means such as an electrical resistance by means of a conducting filament 44 which may be contained in the fastener or integral to the heating apparatus. Once the fastener reaches a suitable temperature and the stressed are relieved, the outer diameter expands to frictionally engage the walls of the hole 36 formed in the bone fragment 35.

By annealing the fastener 10, the shank portion expands or dilates without deformation or melting and as a result the tissue surrounding the bore 36 in the bone fragment 35 is subjected to a lower temperature thereby preventing thermal necrosis. This promotes faster healing of the bone fractures.

While the invention has been described in its presently preferred form, it is to be understood that there are numerous applications and implementations for the present invention. Accordingly, the invention is capable of modification and changes without departing from the spirit of the invention as set forth in the appended claims.

What is claimed is:

1. A fastener adapted for securing a fixation plate having an opening therethrough to a bore formed in a bone, said fastener comprising:

a head engaging a portion of the opening in the fixation plate; and an elongated shank extending from said head, said shank portion and said head portion having a hole, said shank disposed in the bore and being constructed of bioresorbable polymer, said bioresorbable polymer having uni-axial longitudinal stresses formed therein which when heated by a filament inserted into said hole in said head portion and said shank portion, said stresses in said bioresorbable polymer are relieved whereby said shank expands to frictionally secure said shank in the bore without deforming said bioresorbable polymer.

2. The fastener as claimed in claim 1 wherein said bioresorbable polymer is a non-reinforced lactide and glycolide copolymer composition.

3. The fastener as claimed in claim 1 wherein said bioresorbable polymer is heated to a temperature which dilates the periphery of said shank to radially expand and engage the walls of the bore without substantially deforming said bioresorbable polymer and preventing thermal necrosis.

4. The fastener as claimed in claim 1 wherein said shank portion having an outer diameter, said outer diameter being smaller than an inner diameter of the bore which when heated, said outer diameter expands to create a frictional lock in the bore.

5. The fastener as claimed in claim 1 wherein said bioresorbable polymer is heated to a temperature which relieves the unaxial stress and dilates the periphery of said shank to expand absent substantial deformation of said bioresorbable polymer.

6. A fastener adapted for use to secure an osteosynthesis plate having an opening therethrough to a bore formed in a bone, said fastener comprising:

a blank having a shank portion and a head portion, said shank portion and said head portion having a hole, said head portion having a first diameter, said shank portion having a second diameter, said first diameter being larger than said second diameter, said blank being formed of a resorbable material, said shank portion having uni-axial longitudinal stresses formed therein, said stresses formed by pulforming, said head portion further engaging a portion of the opening in the plate;

whereby when said blank is heated by a filament inserted into said hole in said head portion and said shank portion, said uniaxial stresses are relieved, said shank portion expands radially to frictionally secure said shank in the bore in the bone without melting said blank.

7. The fastener as claimed in claim 6 wherein said resorbable material is a non-reinforced lactide and glycolide copolymer composition.

8. The fastener as claimed in claim 6 wherein said shank portion is dilated by heating the material.

9. The fastener as claimed in claim 6 wherein said shank portion is annealed by heat without substantially deforming said shank.

10. The fastener as claimed in claim 6 wherein said uniaxial stresses are altered and said second diameter dilates without melting said blank and reducing thermal necrosis in tissue near the bore.

11. The fastener as claimed in claim 6 wherein said shank is annealed to permit said second diameter to expand radially to frictionally engage the wall of the bore.

12. A method for securing a osteosynthesis plate having at least one opening to at least one bone portion having a bore, said method comprising;

extruding a polymeric material;

pulforming said extruded polymeric material to form a fastener, said pulforming step inducing uniaxial longitudinal stress in said fastener, said fastener having a shank that defines a hole;

positioning the osteosynthesis plate so that the opening in the plate is substantially coaxial with the bore;

disposing said fastener into the substantially coaxial bore so that said shank extends into the bore in the bone portion; and heating said fastener with a filament inserted into said hole to relieve uniaxial stresses in said shank whereby said shank expands to frictionally secure said shank in the bore without deforming said polymeric material.

13. The method as claimed in claim 12 wherein said polymeric material is a non-reinforced lactide and glycolide copolymer composition.

14. The method as claimed in claim 12 wherein said fastener includes a head, said head being larger radially than said shank.

15. The method as claimed in claim 12 wherein said polymeric material is a bioresorbable material.

16. The method as claimed in claim 12 wherein said heating includes heating said fastener to a temperature so that the periphery of said shank is stress relieved and expands radially whereby said fastener frictionally engages the bore and secures the plate to the bore.

17. The method as claimed in claim 12 wherein said heating includes heating said fastener to an annealing temperature to dilate the periphery of said shank without melting said material thereby preventing thermal necrosis.

* * * * *